(12) United States Patent
Zhu et al.

(10) Patent No.: US 9,029,420 B2
(45) Date of Patent: May 12, 2015

(54) AGOMELATINE AND PHARMACEUTICAL COMPOSITIONS THEREOF

(75) Inventors: Jianqiang Zhu, Tianjin (CN); Qingson Tian, Tianjing (CN); Jian Zhao, Tianjin (CN)

(73) Assignee: Tianjin Taipu Pharmaceutical Science & Technology Development Co., Ltd., Tianjin (CN)

( * ) Notice: Subject to any disclaimer, the term of this patent is extended or adjusted under 35 U.S.C. 154(b) by 304 days.

(21) Appl. No.: 13/504,769

(22) PCT Filed: Dec. 13, 2010

(86) PCT No.: PCT/CN2010/002026
§ 371 (c)(1),
(2), (4) Date: Apr. 27, 2012

(87) PCT Pub. No.: WO2011/075943
PCT Pub. Date: Jun. 30, 2011

(65) Prior Publication Data
US 2012/0252901 A1    Oct. 4, 2012

(30) Foreign Application Priority Data
Dec. 23, 2009  (CN) .......................... 2009 1 0245029

(51) Int. Cl.
C07C 233/18   (2006.01)
A61K 31/165   (2006.01)
C07C 231/24   (2006.01)

(52) U.S. Cl.
CPC ........... *C07C 231/24* (2013.01); *C07B 2200/13* (2013.01); *C07C 233/18* (2013.01); *A61K 31/165* (2013.01)

(58) Field of Classification Search
CPC ..................................................... A61K 31/165
USPC ......................................................... 514/630
See application file for complete search history.

(56) References Cited

U.S. PATENT DOCUMENTS 5,194,614 A   3/1993   Andrieux et al.
5,225,442 A   7/1993   Andrieux et al.
(Continued)

FOREIGN PATENT DOCUMENTS

AU    2006203336 A1   2/2007
AU    2006203340 B2   7/2012
(Continued)

OTHER PUBLICATIONS

English translation of U.S. Appl. No. 61/353,266 (2010).*
(Continued)

*Primary Examiner* — Bong-Sook Baek
(74) *Attorney, Agent, or Firm* — Harness, Dickey & Pierce, P.L.C.

(57) ABSTRACT

Agomelatine crystal, which is a drug for treating depression, and pharmaceutical compositions thereof are provided. The X-ray powder diffraction spectra of such agomelatine crystal, which is irradiated by Cu-Kα and showed by 2θ(degree), has characteristic diffraction peaks at 12.84, 13.84, 16.14, 18.56, 19.12, 20.86, 21.20, 23.84; its IR absorption pattern has characteristic absorption peaks at about 3234, 3060, 2940, 1638, 1511, 1436, 1249, 1215, 1184, 1032, 908, 828, 755, 588 cm-1, and its DSC endothermic transition temperature is 97.6° C. The use of the agomelatine crystal as an active ingredient in preparing a medicament for the treatment of depression is also provided.

7 Claims, 4 Drawing Sheets

(56) References Cited

U.S. PATENT DOCUMENTS

| | | | |
|---|---|---|---|
| 5,318,994 A | 6/1994 | Andrieux et al. | |
| 7,250,531 B2 * | 7/2007 | Souvie et al. | 564/172 |
| 7,892,575 B2 | 2/2011 | Julien et al. | |
| 8,067,639 B2 | 11/2011 | Coquerel et al. | |
| 8,252,957 B2 | 8/2012 | Martins et al. | |

FOREIGN PATENT DOCUMENTS

| | | |
|---|---|---|
| AU | 2006203342 B2 | 7/2012 |
| CN | 1680284 A | 10/2005 |
| CN | 1907957 A | 2/2007 |
| CN | 1907959 A | 2/2007 |
| CN | 1981752 A | 6/2007 |
| CN | 101041629 A | 9/2007 |
| CN | 101429134 A | 5/2009 |
| CN | 101781226 A | 7/2010 |
| CN | 101792400 A | 8/2010 |
| EP | 0 447 285 A1 | 9/1991 |
| EP | 1752445 A1 | 2/2007 |
| EP | 1800669 A1 | 6/2007 |
| EP | 2151430 A1 | 2/2010 |
| EP | 2319827 A1 | 5/2011 |
| JP | H0748331 A | 2/1995 |
| JP | 2007051141 A | 3/2007 |
| JP | 2007056017 A | 3/2007 |
| JP | 2009137943 A | 6/2009 |
| WO | WO-2011154140 A2 | 12/2011 |

OTHER PUBLICATIONS

Extended European Search Report regarding Application No. 10838509.7-1454 / 2474522, dated Feb. 18, 2013.

Mino R. Caira. "Crystalline Polymorphism of Organic Compounds." Topics in Current Chemistry, vol. 198. Springer Verlag Berlin Heidelberg 1998.

Sai-Li Zheng et al. "Structures of Polymorphic Agomelatine and Its Cocrystals with Acetic Acid and Ethylene Glycol." Crystal Growth & Design Article. 2011, vol. 11, pp. 466-471. Published on Web Jan. 6, 2011.

Tinant, B. and DeClercq, J.P., "N[42-(7-Methoxy-1-naphthyl)ethyl]-acetamide, a Potent Melatonin Analog", Acta Cryst. (1994), C50, pp. 907-910.

Depreux, P., et al., "Synthesis and Structure—Activity Relationships of Novel Naphthalenic and Bioisosteric Related Amidic Derivatives as Melatonin Receptor Ligands", J. Med. Chem. 1994, 37, 3231-3239.

International Search Report (in English) for PCT/CN2010/002026, mailed Mar. 24, 2011; ISA/CN.

* cited by examiner

Peak search

| Sample | : AG-5-4 | | File | : D/Max-2500.9766 | | Comment | : CuKa 40KV 100mA | | |
|---|---|---|---|---|---|---|---|---|---|
| Date | : 23-Apr-09 09:25 | | Operator | : rigakudmax | | | | | |

| Peak No. | 2Theta | FWHM | d-value | Intensity | I/Io | Peak No. | 2Theta | FWHM | d-value | Intensity | I/Io |
|---|---|---|---|---|---|---|---|---|---|---|---|
| 1 | 5.820 | 0.141 | 15.1720 | 1119 | 6 | 31 | 30.120 | 0.212 | 2.9646 | 2462 | 12 |
| 2 | 9.340 | 0.180 | 9.2631 | 3435 | 17 | 32 | 30.420 | 0.141 | 2.9358 | 1565 | 8 |
| 3 | 9.860 | 0.188 | 8.9632 | 2732 | 14 | 33 | 30.860 | 0.329 | 2.8933 | 1351 | 7 |
| 4 | 10.380 | 0.212 | 8.5317 | 1935 | 10 | 34 | 31.720 | 0.212 | 2.8186 | 1114 | 6 |
| 5 | 11.620 | 0.141 | 7.6092 | 1213 | 6 | 35 | 32.940 | 0.235 | 2.7169 | 779 | 4 |
| 6 | 11.900 | 0.212 | 7.4308 | 2566 | 13 | 36 | 33.700 | 0.212 | 2.6574 | 1044 | 5 |
| 7 | 12.840 | 0.212 | 6.8868 | 4947 | 25 | 37 | 35.300 | 0.282 | 2.5405 | 805 | 4 |
| 8 | 13.840 | 0.188 | 6.3933 | 4618 | 23 | 38 | 36.520 | 0.235 | 2.4584 | 641 | 3 |
| 9 | 15.200 | 0.212 | 5.8241 | 2188 | 11 | 39 | 37.640 | 0.329 | 2.3878 | 631 | 3 |
| 10 | 16.140 | 0.212 | 5.4870 | 7348 | 37 | 40 | 38.800 | 0.165 | 2.3190 | 673 | 3 |
| 11 | 16.820 | 0.212 | 5.2667 | 1184 | 6 | | | | | | |
| 12 | 17.340 | 0.282 | 5.1099 | 2729 | 14 | | | | | | |
| 13 | 18.560 | 0.188 | 4.7767 | 19920 | 100 | | | | | | |
| 14 | 19.120 | 0.188 | 4.6300 | 5360 | 27 | | | | | | |
| 15 | 19.840 | 0.165 | 4.4713 | 1151 | 6 | | | | | | |
| 16 | 20.060 | 0.188 | 4.2549 | 14061 | 75 | | | | | | |
| 17 | 21.200 | 0.212 | 4.1874 | 6023 | 30 | | | | | | |
| 18 | 21.960 | 0.188 | 4.0442 | 1574 | 8 | | | | | | |
| 19 | 22.280 | 0.188 | 3.9868 | 1685 | 8 | | | | | | |
| 20 | 22.940 | 0.235 | 3.8736 | 1675 | 8 | | | | | | |
| 21 | 23.840 | 0.259 | 3.7293 | 12802 | 64 | | | | | | |
| 22 | 24.220 | 0.165 | 3.6717 | 3040 | 15 | | | | | | |
| 23 | 25.220 | 0.188 | 3.5293 | 1202 | 6 | | | | | | |
| 24 | 25.780 | 0.235 | 3.4529 | 2213 | 11 | | | | | | |
| 25 | 27.040 | 0.165 | 3.2940 | 1045 | 5 | | | | | | |
| 26 | 27.540 | 0.165 | 3.2361 | 1178 | 6 | | | | | | |
| 27 | 27.880 | 0.282 | 3.1974 | 1183 | 6 | | | | | | |
| 28 | 28.260 | 0.188 | 3.1553 | 1463 | 7 | | | | | | |
| 29 | 28.540 | 0.165 | 3.1250 | 1903 | 10 | | | | | | |
| 30 | 29.300 | 0.282 | 3.0456 | 2765 | 14 | | | | | | |

Figure 1-a

AGOMELATINE AND PHARMACEUTICAL COMPOSITIONS THEREOF

CROSS-REFERENCE TO RELATED APPLICATIONS

This application is a 371 U.S. National Stage of International Application No. PCT/CN2010/002026, filed Dec. 13, 2010, and claims priority to Chinese Patent Application No. 200910245029.5, filed Dec. 23, 2009, the disclosures of which are herein incorporated by reference in their entirety.

FIELD OF THE INVENTION

The present invention belongs to the field of chemical synthesis of drugs. And the present invention relates to the crystal of agomelatine and the preparation method thereof, as well as the use of the agomelatine crystal as active ingredient in manufacturing a medicament for the treatment of depression.

BACKGROUND OF THE INVENTION

With the development of social economy, the speeding-up of life pace and the increases of emotional impact, the incidence of depression increased year by year. Depression which is one main type of mood disorders, is a syndrome characterized by significant and long-lasting depressed mood. Its main symptoms are depressed mood, decreased interest, pessimism, retardation of thinking, lack of initiative, self-blame from sin, poor diet and sleep, worry of suffering from various diseases, feeling of multiple discomforts, and in severe cases, suicidal thoughts and behaviors may occur. Clinically, the treatment of depression mainly relies on Western medicines, however, they all have varying degrees of side effect and dependence, though they are effective to some extent.

Agomelatine is the first and the only melatonin 1, 2(MT1 MT2) receptors agonist developed by Servier (France), and it is also a serotonin 2c (5HT2c) receptor antagonist. It is mainly used for the treatment of the onset of depression. The unique mechanism of agomelatine is completely different from that of the antidepressants which are widely used at present, such as selective serotonin reuptake inhibitor (SSRI) and serotonin-noradrenaline reuptake inhibitor (SNRI): SSRI and SNRI antidepressants achieve their antidepressant effects through increasing the concentration of serotonin, but this also brings about various side effects, such as weight changes, sexual dysfunction, withdrawal syndrome, and the like. The molecular structure of agomelatine directly binds to the serotonin 2c (5HT2c) receptor in the neural postsynaptic membrane in order to exert its antidepressant efficacy without increasing the serotonin concentration in the synaptic cleft. This unique mechanism makes agomelatine exert its antidepressant efficacy rapidly and effectively together with avoiding side effects of the drug to a maximal extent.

Another unique target of agomelatine involves the melatonin receptor. MT1 and MT2 receptors are densely distributed on human suprachiasmatic nucleus, which is in charge of human sleeping rhythm. Agomelatine is an agonist of MT1 and MT2 receptors. Through its agonistic effect on MT1 and MT2 receptors, the sleeping quality of patients would be well improved, and the waking state of patients would be improved during the daytime. There is a mutually causal relationship between the quality of sleep and the outcome of depression. It is reported that problems of sleeping disorders exist in 80% of depression patients. The improvement of sleeping quality directly promotes the improvement of general clinical states of depression patients. A large number of clinical studies have confirmed that agomelatine have ideal long and short term efficacies. It rapidly achieves efficacy and significantly reduces the relapse and recrudescence rates in depression patients, and the safety is significantly better than that of SSRI and SNRI drugs. In addition, it significantly improves sleeping quality of patients and the waking state during daytime together with reliving the core symptom of depression. It is no doubt that the creation of agomelatine brings about a new option in the treatment of depression for doctors and patients.

Chemical name of agomelatine is N-[2-(7-methoxy-1-naphthyl)-ethyl]acetamide with the structural formula below:

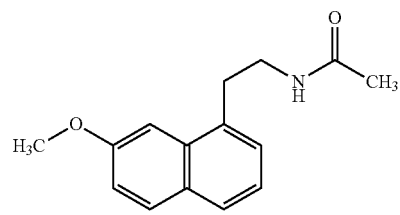 [SMILES: COc1ccc2cccc(CCNC(C)=O)c2c1]

Agomelatine has been reported in several documents. For example, agomelatine, the preparation and the therapeutic use thereof are described in European Patent Specification EP0447285. A new synthetic method, a new crystal form of agomelatine and the pharmaceutical composition thereof are described in Chinese Patent CN1680284. A new crystal form VI of agomelatine, the preparation method thereof and pharmaceutical composition containing thereof are described in Application No. 200810174918.2. Another synthetic route of agomelatine is described in EP0447285; J.M.C,1994,37, 3231-3239.

As well known, compounds may be present in two or more crystalline states, which is a natural property of a substance. The molecules having the same structure are crystallized into different solid forms which are known as homogeneous polycrystalline. Different kinds of crystals have different lattice energy, thus they exhibit physical properties of excellent purity and well reproducible. Taking advantage of a different preparation method, the present invention obtained a novel crystal of agomelatine which is different from those reported in the prior art, and the present invention is completed by obtaining X-ray powder diffraction spectra.

SUMMARY OF THE INVENTION

One objective of the present invention is to provide a crystal of agomelatine, which is of good quality and reproducibilty. The purity thereof may be more than 99% in normalization method using HPLC.

Another objective of the present invention is to provide a method of preparing the crystal of agomelatine.

Another objective of the present invention is to provide a pharmaceutical composition containing the agomelatine crystal.

A further objective of the present invention is to provide the use of agomelatine crystal composition in manufacturing a medicament for the treatment of depression. In order to achieve above-mentioned objectives, the present invention provides the following technical solutions:

A crystal of agomelatine is provided, which is characterized by X-ray powder diffraction pattern in the 2θ using Cu-Kα radiation as shown in FIG. 1. The IR absorption pattern thereof has characteristic absorption peaks at about 3234, 3060, 2940, 1638, 1511, 1436, 1249, 1215, 1184, 1032, 908, 828, 755, 588 cm$^{-1}$, and DSC shows an endothermic transition at 97.6□.

The agomelatine crystal according to the present invention is characterized by typically characteristic diffraction peaks at 12.84, 13.84, 16.14, 18.56, 19.12, 20.86, 21.20, 23.84 X-ray powder diffraction pattern in the 2θ using Cu-Kα radiation.

The method of preparing agomelatine crystal according to the present invention is as follows: crude agomelatine is dissolved in DMF, filtered and the filtrate is poured into distilled water with rapid stirring and maintained for 15-45 min. It is filtered and vacuum-dried to obtain agomelatine crystal with the content being more than 99%. For example, a certain amount of crude agomelatine is added into DMF to form a solution in DMF, filtered and the filtrate is poured into distilled water with rapid stirring and maintained for 15-45 min. It is filtered and vacuum-dried to obtain agomelatine crystal with the content being more than 99%.

It should be understood by the skilled in the art that the addition of crude agomelatine into DMF is generally accomplished at room temperature. In some cases, however, the temperature may be also appropriately raised as required, with the proviso that the crude agomelatine can be completely dissolved. Generally, the vacuum-drying may be accomplished at room temperature or at appropriately raised temperature as required to remove water with the purpose of assuring the content of agomelatine crystal being greater than 99%. No particular requirement according to the present invention is present in terms of the time for vacuum-drying, which can be adjusted according to the measured results of content of agomelatine crystal, and normally, is 5-10 h.

There is no special requirement for the volume of DMF, with the proviso that the crude agomelatine can be dissolved. And the filtrate is generally poured into distilled water with rapid stirring at 5-60° C.

The weight ratio of the filtrate (DMF solution) to the distilled water according to the present invention is 1:20-50, preferably 1:20-40, and more preferable 1:20-30.

In one exemplary example of the present invention, crude agomelatine is added into DMF, dissolved at 25° C., and filtered. At room temperature, the filtrate is poured into 200 ml distilled water at 5° C. with rapid stirring. Subsequently, the solution is mixed and filtered at room temperature. The filter cake is washed by distilled water and vacuum-dried to obtain agomelatine crystal with content greater than 99%.

In another exemplary example of the present invention, crude agomelatine is added into DMF, and filtered. At room temperature, the filtrate is poured into 250 ml distilled water at 15° C. with rapid stirring. Subsequently, the solution is mixed and filtered at room temperature. The filter cake is washed by distilled water and vacuum-dried to obtain agomelatine crystal with content greater than 99%.

In yet another exemplary example of the present invention, crude agomelatine is dissolved in DMF and filtered. At room temperature, the filtrate is poured into 500 ml distilled water at 25° C. with rapid stirring. Subsequently, the solution is mixed and filtered at room temperature. The filter cake is washed by distilled water and vacuum-dried to obtain agomelatine crystal with content greater than 99%.

In a further exemplary example of the present invention, crude agomelatine is added into DMF and filtered. At room temperature, the filtrate is poured into 800 ml distilled water at 60° C. with rapid stirring. Subsequently, the solution is mixed and filtered at room temperature. The filter cake is washed by distilled water and vacuum-dried to obtain agomelatine crystal with content greater than 99%.

The agomelatine crystal prepared according to the present invention is characterized by:

1. X-Ray Powder Diffraction:
Instruments: Rigaku, Japan, D/MAX 2500 X-ray diffractometer
Target: Cu-Kα radiation (λ=1.5405), 2θ=2-40° C.
Step angle: 0.04° C.
Calculated time: 0.5 s
Tube voltage: 40 KV
Tube current: 100 mA
Scanning speed: 8° C./min
Filter: Graphite monochromator
Error of 2θ value: 2θ value±0.10

TABLE 1

(See FIG. 1 and FIG. 1-a for details)

| 2 θ | I/I$_0$ |
|---|---|
| 12.84 | 25 |
| 13.84 | 23 |
| 16.14 | 37 |
| 18.56 | 100 |
| 19.12 | 27 |
| 20.86 | 75 |
| 21.20 | 30 |
| 23.84 | 64 |

2. Instrument Model and Test Conditions:
METTLER TOLEDO DCC822 differential scanning calorimeter; temperature range: room temperature 40-300° C.; heating rate: 10° C./min.
The results indicate that the DSC endothermic transition is at 97.6° C.

3. Infrared Spectroscopy (IR):
Instruments: Nicolet, US, MAGNA-560 Fourier transform infrared spectrometer.
The wave numbers of IR spectrum for the agomelatine crystal according to the present invention using potassium bromide for grinding are as follows: characteristic absorption peaks at 3234, 3060, 2940, 1638, 1511, 1436, 1249, 1215, 1184, 1032, 908, 828, 755, 588 cm$^{-1}$.

The desirable dosage can be easily determined by the skilled in the art, and such dosage can be altered according to the delivery route, the concentration of the formulation for the agomelatine crystal and the progression of disease. Furthermore, the age, body weight, diet, the time of administration and the like for the specific patient may also lead to the appropriate adjustment of the dosage.

The present invention further discloses a pharmaceutical composition containing a pharmaceutically effective amount of agomelatine crystal and one or more pharmaceutically acceptable carriers. Wherein said composition is oral formulation or injection, preferably oral formulation, for example tablet, capsule, granule, oral liquid and the like. Agomelatine crystal and pharmaceutically acceptable carriers can also be mixed to form lyophilized powder and the like.

Said one or more pharmaceutically acceptable carriers according to the present invention include: stabilizer, diluent, disintegrating agent, solvent, adhesive and lubricant, etc. Wherein the diluent includes, but is not limited to, starch, microcrystalline cellulose, polyethylene glycol-1000, polyethylene glycol-4000, polyethylene glycol-6000, sucrose, dextrin, lactose, powdered sugar, glucose, dextran with a low molecular weight, sodium chloride or mannitol, etc. Said adhesive includes, but is not limited to, water, ethanol, starch paste, syrup, gelatin, methyl cellulose, hydroxypropyl methyl cellulose, sodium carboxymethyl cellulose, sodium alginate or polyvinylpyrrolidone, etc. Said lubricant includes, but is not limited to, magnesium stearate, stearic acid, boric acid, sodium chloride, sodium oleate, sodium laurylsulfate, poloxamer and the like. Said disintegrating agent includes, but is not limited to, starch, sodium carboxymethyl starch, sodium bicarbonate and citric acid, tartaric acid or low-substituted hydroxypropyl cellulose and the like. Said stabilizer includes, but is not limited to, polysaccharide such as agar, acrylic resin, cellulose ether and carboxymethyl cellulose and the like.

The present invention further discloses the use of the agomelatine crystal which is obtained by the above-mentioned preparation method as an active ingredient in manufacturing a medicament for the treatment of depression. The agomelatine crystal discovered in the present invention has the same use with the known agomelatine compound per se. For example, it can be used to treat depression, severe depression, seasonal affective disorder, sleep disorders, cardiovascular pathology, insomnia caused by time difference and depression caused by fatigue, and so on. As another example, the obtained agomelatine crystal is subjected to pharmacological and pharmacodynamic studies, the results show that the agomelatine crystal has good therapeutic effects for central neural system and microcirculation.

Compared to known crystalline forms, the agomelatine crystal prepared in the present invention has advantageous effects as follows:

The agomelatine crystal prepared in the present invention is a novel crystal containing no water or any other solvent. It exhibits valuable characteristics in the aspects of dissolution, mobility and preparation of formulation. And it has advantages of high quality, good solubility, favorable absorption, stability to temperature, light, humidity in long storage time, and the like.

DETAILED DESCRIPTION OF THE INVENTION

Figure 1:
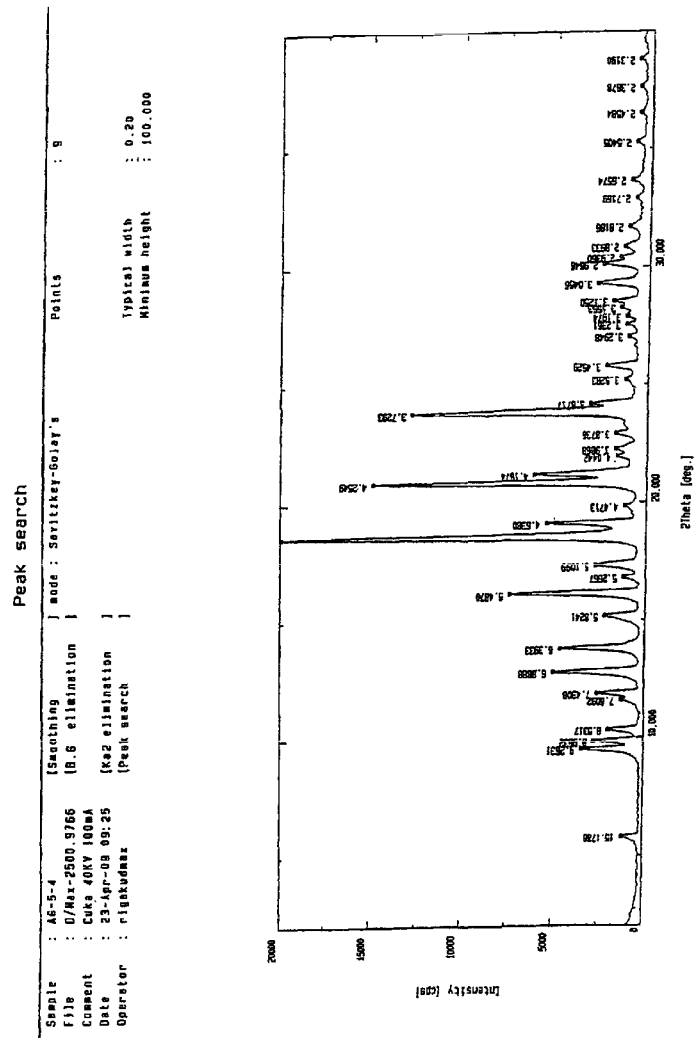
FIG. 1 and FIG. 1-a are X-ray powder diffraction spectra of the agomelatine crystal.
Figure 2:
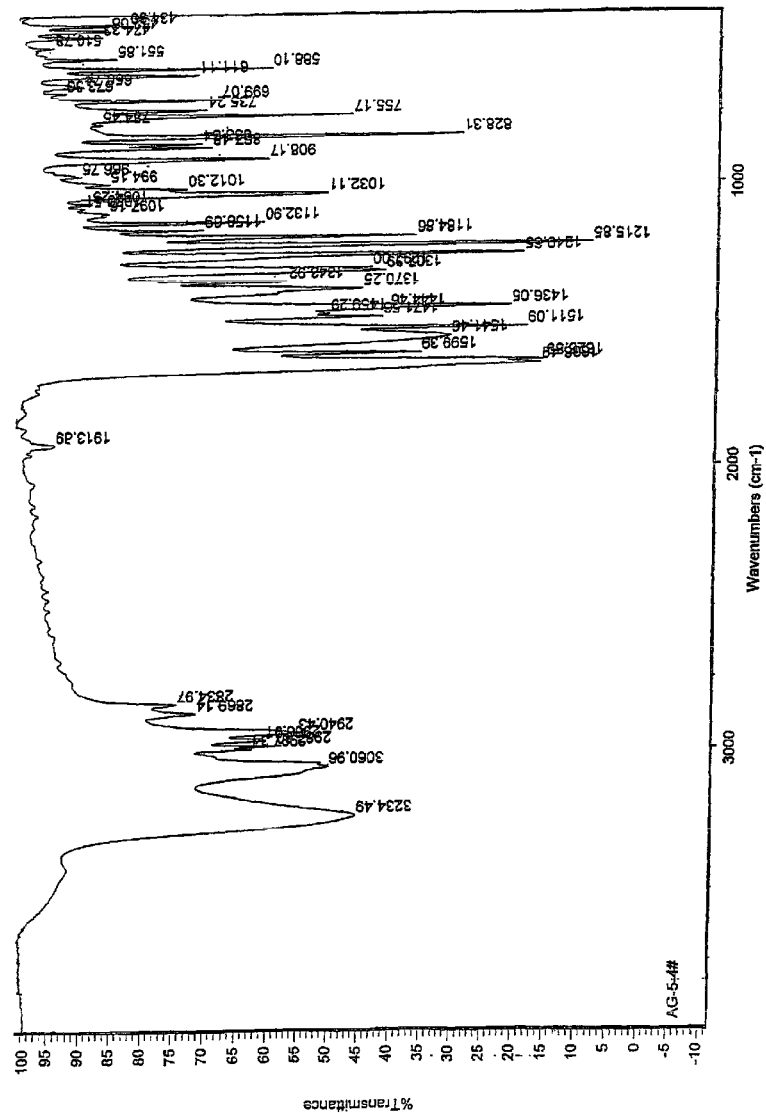
FIG. 2 is IR spectrum of the agomelatine crystal.
Figure 3:
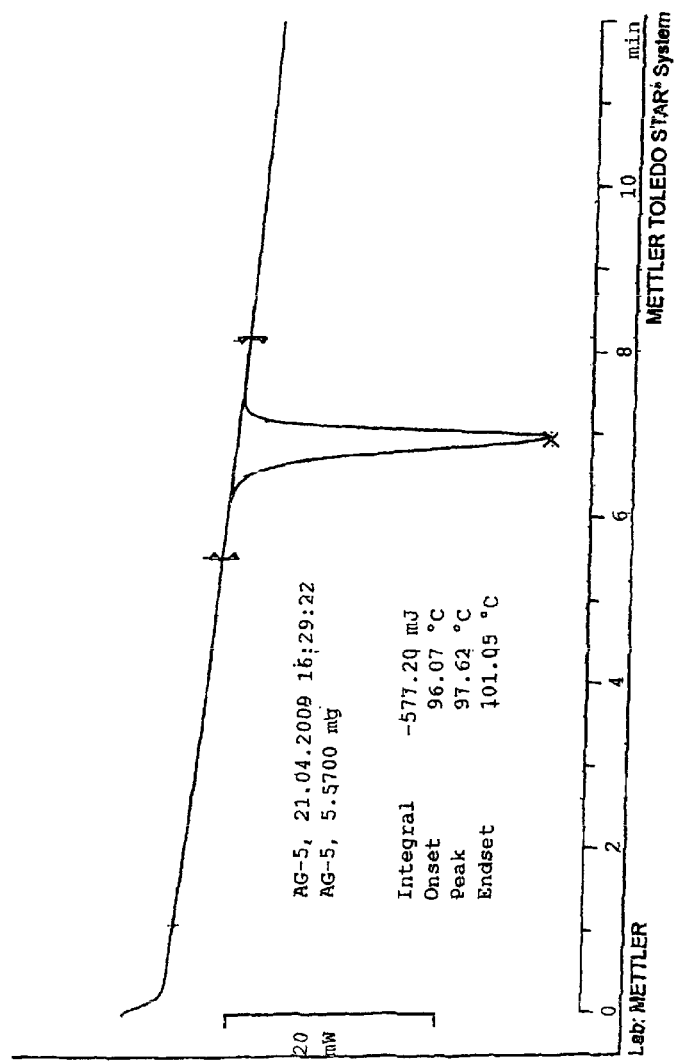
FIG. 3 is DSC endothermic transition spectrum of the agomelatine crystal.

The following examples are facilitated to understand the present invention, but it is not and should not be construed as limiting the scope of the invention in any way. And CN1680284 is referred to for the preparation of the crude agomelatine.

Reference Example 1

The Preparation of ethyl(7-methoxy-1,2,3,4-tetrahydro-1-naphthalenyl)-acetate 85 g 7-methoxy-1-tetralone and 75 g activated zinc powder were added into a reaction flask. Then, 100 ml toluene and 2 iodine crystals were added, mixed and heated to reflux state. A mixed solution of 129 ml ethyl bromoacetate and 100 ml toluene was subsequently added in drops slowly and heated. The reaction solution was maintained in reflux state. After adding in drops, the reaction solution was kept in reflux for further 10 min before stopping the reaction.

The reaction solution was cooled to 25° C., and 1500 ml ice water and 200 ml hydrochloric acid were added with stirring. The solution was stratified after stirring for 10 minutes. The aqueous layer was extracted by 250 ml×2 toluene, and the organic phase was combined and dried by adding 70 g anhydrous sodium sulfate. On the next day, they were filtered and 80 g $P_2O_5$ was added into the filtrate. Then, the filtrate was mixed and heated to reflux for 3 hours. After completion of the reaction, it was cooled to 25° C. and filtered. The filtrate was vacuum evaporated to obtain 100 g light brown oil with 90% content (HPLC), and the yield is 75.8%.

Reference Example 2

The Preparation of ethyl(7-methoxy-1-naphthyl)-acetate 17.6 g sulfur and 90 g ethyl (7-methoxy-1,2,3,4-tetrahydro-1-naphthalenyl)-acetate were added into the reaction flask and heated to 215° C. with stirring. The reaction was carried out for 10 hours. After completion of the reaction, the reaction system was cooled to 60° C. 500 ml ethyl acetate was added and the mixture was stirred for 30 minutes. The mixture was filtered and the filter cake was washed with 100 ml ethyl acetate. Then, the filtrate was combined and vacuum evaporated to obtain 92 g brown oil with 82.4% content (HPLC). The yield is 85%.

Reference Example 3

The Preparation of 7-methoxy-1-naphthaleneacetic acid 40 g sodium hydroxide was dissolved in 1000 ml water and 1000 ml 95% ethanol was added. They were mixed. Then, 50 g ethyl (7-methoxy-1-naphthyl)-acetate was added into above-mentioned mixture solution and the mixture solution was stirred for 3 hours at room temperature. The reaction was subsequently stopped and vacuum evaporated to remove ethanol, resulting in brown-red liquid. The liquid was washed with 300 ml×2 ethyl acetate prior to adding 30 ml 95% ethanol into the aqueous layer. The pH was adjusted to 2 by adding concentrated hydrochloric acid in drops with rapid stirring, resulting in a large amount of light brown solid being precipitated. They were filtered and dried to obtain 32 g product with mp of 154-156° C. The content measured by HPLC is 98.48%, and the yield is 72%.

Reference Example 4

The Preparation of 7-methoxy-1-naphthaleneacetamide 50 g 7-methoxy-1-naphthaleneacetic acid was added into 750 ml dichloromethane and heated to dissolve the same. Thionyl chloride was slowly added in drops while kept in reflux state. The reaction was refluxed for further 2 h after the completion of addition.

After completion of the reaction, the reaction solution was vacuum evaporated to obtain brown-red oil. It was cooled to solidify by external ice water. The obtained solid was dissolved in 500 ml ethyl acetate, and cooled by external ice saline. 47.2 ml ammonia water was slowly added in drops, resulting in a large amount of light yellow solid being precipitated. It was filtered and dried to obtain 49.8 g crude product. Recrystallization was carried out by using 747 ml 95% ethanol and 37.3 g activated carbon to obtain 46 g refined product with the mp of 201-202° C. The yield is 92.4%.

Reference Example 5

The Preparation of 7-methoxy-1-naphthaleneacetonitrile 30 g 7-methoxy-1-naphthaleneacetamide, 120 ml THF and 35.7 g triethylamine were added into reaction flask. The mixture was stirred and cooled with external ice saline bath. Trifluoroacetic anhydride was slowly added in drops. After completion of addition, it was stirred for further 15 min. Then, the ice bath was removed and stirring was carried out for 2 h at room temperature. After completion of the reaction, the reaction solution was evaporated. Subsequently, 200 ml water was added and the solution was filtered and dried after stirring for 0.5 hours, to obtain 28 g crude product. Recrystallization was carried out using 280 ml isopropyl ether and 1.4 g activated carbon to obtain 22 g refined product with the mp of 82-84° C. The yield is 80%.

Reference Example 6

The Preparation of 2-(7-methoxy-1-naphthyl)ethylamine 56 g 7-methoxy-1-naphthaleneacetonitrile, 120 ml ammonia water, 332 ml 95% ethanol, 20 g Raney-Ni were added into autoclave. $H_2$ was introduced after vacuuming it. The operation was repeated for 3 times. The reaction was stirred for 12 hours while $H_2$ was introduced and the condition of 300 atm and 60° C. was maintained. After completion of the reaction, the reaction was kept overnight at room temperature. On the next day, it was vacuumed and $N_2$ gas was introduced. The autoclave was opened up, and the reaction solution was filtered to remove the catalyst. The filtrate was vacuum evaporated until dry to obtain 56 g light green oil. The content is measured as 96.95% by HPLC, and the yield is 95%.

Reference Example 7

The Preparation of N-[2-(7-methoxy-1-naphthyl)ethyl]acetamide (Agomelatine)

40 g 2-(7-methoxy-1-naphthyl)ethylamine was dissolved in 250 ml pyridine and heated to 40° C. for complete dissolution. 21.9 g acetyl chloride was slowly added in drops with stirring in ice bath. After completion of addition, the ice bath was removed and the solution was stirred at room temperature for 30 min. Subsequently, the reaction solution was poured into 300 ml ice water together with vigorous stirring, resulting in a large amount of white precipitate being precipitated. The stirring was carried out for another 1 hour. Then, the solution was filtered and the filter cake was washed by 200 ml×2 water to obtain 48 g crude product (which was used in the following preparation examples).

$^1$H NMR (400 MHZ, $CDCl_3$): δ 7.77-7.15 (m, 6H,); δ 5.61 (s, 1H,); δ 3.99 (s, 3H,); δ 3.62 (m, 2H,); δ 3.25 (t, 2H,); δ 1.95 (s, 3H,), which is consistent with that in the literature (J. Med. Chem, 1994, 37(20), 3231-3239).

PREPARATION EXAMPLES

Example 1

2 g crude product of agomelatine was dissolved in 10 ml DMF. The solution was filtered and at room temperature, the filtrate was poured into 300 ml distilled water of 25° C. with rapid stirring. After completion of the addition, the solution was stirred at room temperature, and filtered. The filter cake was washed with distilled water, and the product was dried in vacuum at room temperature, to obtain agomelatine crystal with the content being greater than 99% as measured by HPLC. It is shown in FIG. 1.

Example 2

At room temperature, 1 g crude product of agomelatine was dissolved in 5 ml DMF. The solution was filtered and the filtrate was poured into 210 ml distilled water of 40° C. with rapid stirring. After completion of the addition, the solution was stirred for 20 minutes at room temperature, and filtered. The filter cake was washed with distilled water, and the product was dried in vacuum for 10 hr, to obtain agomelatine crystal with the content being greater than 99% as measured by HPLC. It is shown in FIG. 1.

Example 3

2 g crude product of agomelatine was dissolved in 40 ml DMF. The solution was filtered and at room temperature, the filtrate was poured into 300 ml distilled water of 50° C. with rapid stirring. After completion of the addition, the solution was stirred for 30 minutes at room temperature, and filtered. The filter cake was washed with distilled water, and dried in vacuum, to obtain agomelatine crystal with the content being greater than 99% as measured by HPLC. It is shown in FIG. 1.

Example 4

2 g crude product of agomelatine was dissolved in 10 ml DMF. The solution was filtered and at room temperature, the filtrate was poured into 250 ml distilled water of 5° C. with rapid stirring. After completion of the addition, the solution was stirred for 30 minutes at room temperature, and filtered. The filter cake was washed with distilled water, and the product was dried in vacuum for 8 hr, to obtain agomelatine crystal with the content being greater than 99% as measured by HPLC. It is shown in FIG. 1.

Example 5

2 g crude product of agomelatine was dissolved in 50 ml DMF. The solution was filtered and at room temperature, the filtrate was poured into 400 ml distilled water of 60° C. with rapid stirring. After completion of the addition, the solution was stirred for 45 minutes at room temperature, and filtered. The filter cake was washed with distilled water, and dried in vacuum for 6 hr, to obtain agomelatine crystal with the content being greater than 99% as measured by HPLC. It is shown in FIG. 1.

Example 6

2 g crude product of agomelatine was dissolved in 10 ml DMF. The solution was filtered and at room temperature, the filtrate was poured into 600 ml distilled water of 40° C. with rapid stirring. After completion of the addition, the solution was stirred at room temperature, and filtered. The filter cake was washed with distilled water, and the product was dried in vacuum for 10 hr, to obtain agomelatine crystal with the content being greater than 99% as measured by HPLC. It is shown in FIG. 1.

FORMULATION EXAMPLES

Example 1

25 g agomelatine crystal, 43 g lactose, and 16 g microcrystalline cellulose were evenly mixed. An appropriate amount of 10% hydroxypropyl methyl cellulose solution was added for the granulation. The mixture was dried and then 5.3 g sodium carboxymethyl starch, 1.5 g magnesium stearate were added. They were evenly mixed and compressed into tablets. Then, they were coated, and 1000 tablets were prepared.

Example 2

25 g agomelatine crystal, 397 g lactose, 93 g pregelatinized starch, 15 g hydroxypropyl cellulose, 19.8 g cross-linked sodium carboxymethyl cellulose were evenly mixed. The granulation was carried out using pure water. The granules were dried and compressed into tablets. Then, they were coated, and 1000 tablets were prepared.

Example 3

25 g agomelatine crystal was added into 100 g molten polyethylene glycol 4000. The mixture was stirred until complete dissolution and uniform mixing. The mixture which was maintaining at a constant temperature of 60° C. were added into liquid paraffin (5 to 10° C.) in drops. They were solidified into dropping pills. The liquid paraffin was removed completely, and the pills were sorted to obtain the product.

Example 4

100 g agomelatine crystal, 100 g dextrin and 570 g lactose were mixed. They were granulated with 70% ethanol and dried. The granules were filled into capsules to obtain 1000 capsules.

The invention claimed is:

1. A crystal of agomelatine, which is characterized by X-ray powder diffraction pattern in the 2θ using Cu-Kα radiation as shown in FIG. 1: the infrared (IR) absorption pattern thereof has characteristic absorption peaks at 3234, 3060, 2940, 1638, 1511, 1436, 1249, 1215, 1184, 1032, 908, 828, 755, and 588 cm$^{-1}$, and differential scanning calorimetry (DSC) shows an endothermic transition at 97.6° C.

2. The agomelatine crystal according to claim 1, wherein X-ray powder diffraction pattern in the 2θ using Cu-Kα radiation has characteristic diffraction peaks at 12.84, 13.84, 16.14, 18.56, 19.12, 20.86, 21.20, and 23.84.

3. A method for the preparation of agomelatine crystal according to claim 1, which is characterized by: crude agomelatine is dissolved in dimethylformamide (DMF), filtered and the filtrate is poured into distilled water with rapid stirring and maintained for 15-45 min, subsequently the solution is filtered and dried.

4. The preparation method according to claim 3, wherein the weight ratio of said filtrate to distilled water is 1:20-50.

5. A pharmaceutical composition, which contains a therapeutically effective amount of agomelatine crystal as defined in claim 1, and one or more pharmaceutically acceptable carriers.

6. The pharmaceutical composition of claim 5, wherein said composition is an oral formulation.

7. A method for the treatment of depression, wherein the method comprises administering the agomelatine crystal as defined in claim 1.

* * * * *